United States Patent [19]

Rabenau et al.

[11] Patent Number: 5,451,231
[45] Date of Patent: Sep. 19, 1995

[54] SURGICAL STAPLE REMOVER

[75] Inventors: Richard Rabenau, Birmingham; Larry L. Young, Arab, both of Ala.

[73] Assignee: Ryder International Corporation, Arab, Ala.

[21] Appl. No.: 209,840

[22] Filed: Mar. 11, 1994

[51] Int. Cl.⁶ ............................................. A61B 17/04
[52] U.S. Cl. .................................... 606/138; 81/342; 81/381; 254/28
[58] Field of Search .................. 606/138; 254/28; 81/419, 421, 422, 342, 381

[56]        References Cited
       U.S. PATENT DOCUMENTS

| | | | |
|---|---|---|---|
| 1,956,166 | 4/1934 | Cavanaugh | 254/28 |
| 4,026,520 | 5/1977 | Rothfuss et al. | 254/28 |
| 4,569,505 | 2/1986 | Braun | 254/28 |
| 4,589,631 | 5/1986 | Markus | 254/28 |
| 4,640,274 | 2/1987 | Nakamoto | 81/421 |
| 4,805,876 | 2/1989 | Blake et al. | 254/28 |

*Primary Examiner*—Gary Jackson
*Attorney, Agent, or Firm*—Trexler, Bushnell, Giangiorgi & Blackstone, Ltd.

[57]        ABSTRACT

A surgical staple extractor which has a gripping portion and a pair spaced-apart jaws and an anvil associated with the gripping portion. Structures are provided with the gripping portion for moving the anvil and the jaws in a scissor action to transfer forces from the anvil and jaws to a staple retained therebetween in order to mechanically deform or reform the staple for extraction from a patient. Cams are positioned between the jaws and the anvil for positively camming or displacing the jaws outwardly when the anvil jaws and jaws are operated. Actuation of the gripping portion results in moving the anvil and jaws with the cams interacting between the anvil and jaws for positively displacing the jaws outwardly in relation to the anvil for promoting controlled deformation of the staple in a removal path approximating the entry path thereby disengaging the staple from the patient.

19 Claims, 5 Drawing Sheets

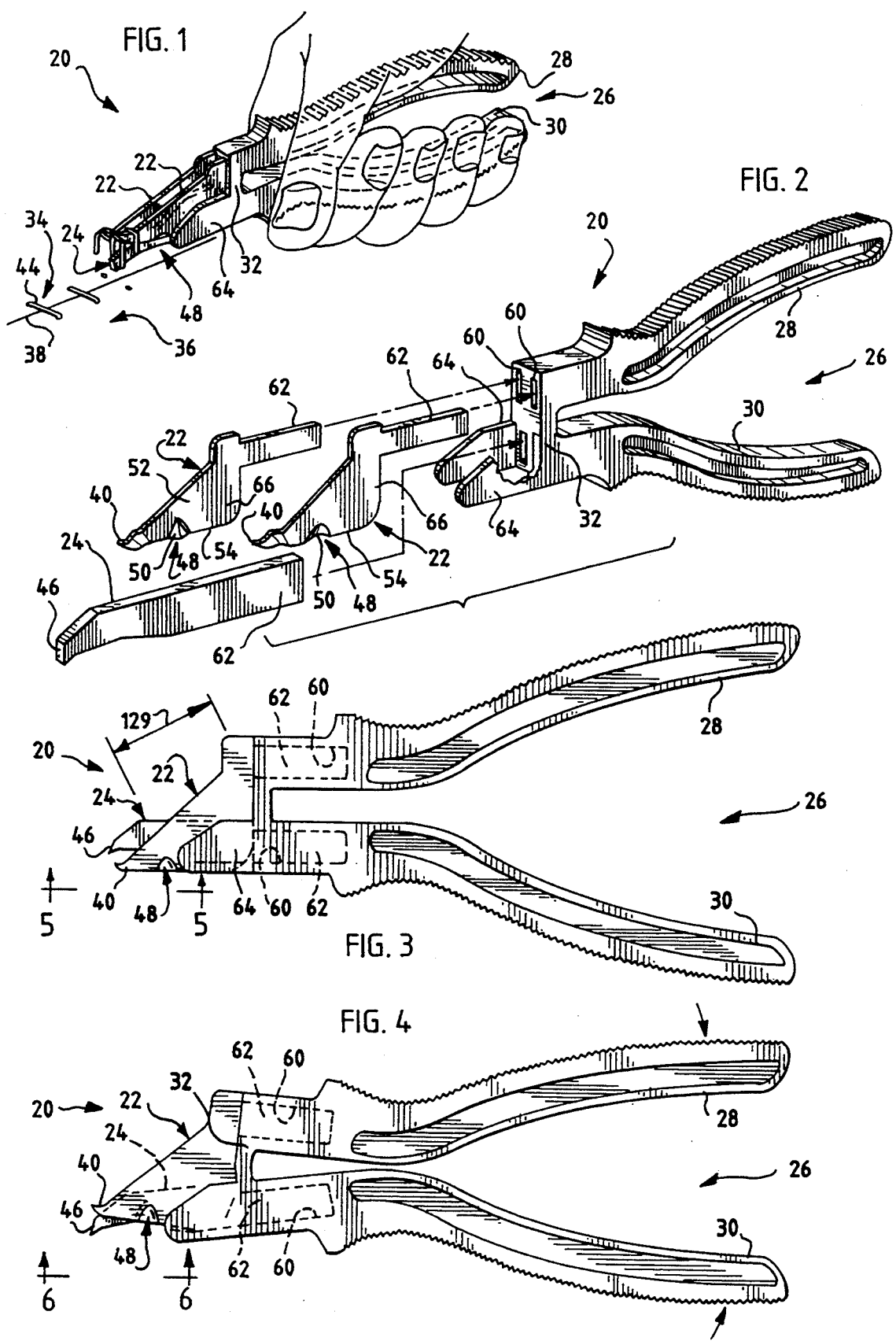

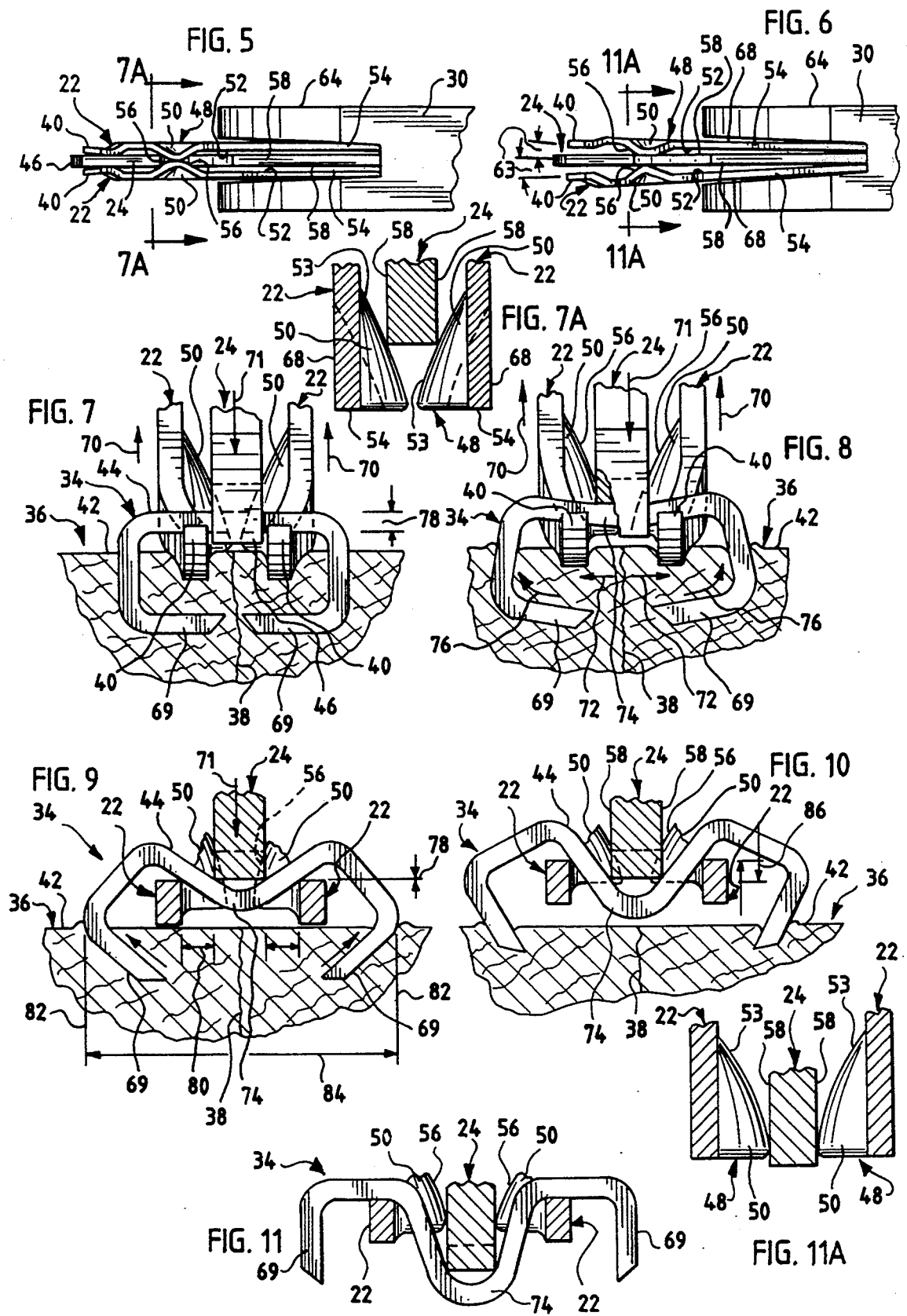

SURGICAL STAPLE REMOVER

BACKGROUND OF THE INVENTION

The present invention relates to surgical staple removers or extractors for extracting surgical staples from a patient.

Surgical staples provide an efficient and secure means for closing a surgical opening at the conclusion of a surgical procedure. Surgical staples have become quite popular with the medical profession for numerous reasons which need not be elaborated on herein. Suffice it to say that the surgical staple is a preferred method of closing surgical sites. The staples must be removed at an appropriate time and thereby create the need for a surgical staple remover to quickly and efficiently remove staples from a patient without injuring the partially healed wound or patient.

A number of surgical staple extractors have been devised which generally function to remove staples from a surgical site. These removers work in a basic scissoring action to deform the staple by driving at least a portion of the staple downwardly between an anvil and two opposed jaws. A problem arises with prior art surgical staple extractors such that the interaction between the anvil, jaws, and staple may scrape the staple material, forming metal filings or shavings which may drop onto or into the surgical site. Furthermore, the force required to actuate or operate the prior art surgical staple extractors is unpredictable and as such may cause problems for the medical professional extracting staples from a patient.

A wide variety of materials are used in the manufacturing of surgical staples. Prior art staple extractors generally do not accommodate the wide variety of staple materials. As such, a given extractor may perform unpredictably when used to extract a staple, the material of which was not considered when designing the extractor. In this regard, the prior art staple extractors may provide either two much rigidity in the jaws or too little rigidity in the jaws.

For example, one form of staple extractor referred to as Proximate staple remover, produced by Ethicon, a Johnson & Johnson company, is formed of a rigid metallic material. The jaws on the Ethicon remover generally provide no outward deflection of the jaws. This type of staple extractor may produce shavings from the staple or may deform the staple in an undesirable manner. Another form of staple extractor produced by Weck Company employs metallic jaws retained on an axle extending from a plastic handle arrangement. The jaws while flexible, are not positively cammed outwardly upon removing a staple, and any flexing which may occur is random and uncontrolled and will occur only after the staple is virtually fully removed. These prior art designs while employing somewhat similar anvil and jaw structures do not utilize the hereafter described cam means and associated structures of the present invention, nor do they teach the novel assembly of the present invention.

As another consideration in staple extracting, it would be desirable to extract the staples by reforming or deforming the staples in approximately the same path in which they were inserted into the patient'issue in the surgical site. In other words, while the prior art staple extractor removes staples frommthe surgical site, they may tend to remove staples in a path which is slightly different from the path in which the staples were inserted. In this regard, the slightly different extraction path will cause tissue trauma or adversely affect the healing incision in the surgical site.

For the forgoing reasons, there is a need for a surgical staple extractor which operates with a predictable operating force, reforms the staple by following a preferred staple reforming path, and controllably spreads the jaws a desired distance.

Summary of the Invention

A general object of the present invention is to provide a surgical staple extractor which controllably spreads jaws associated with the extractor relative to an associated anvil while reforming a staple therebetween during an extraction operation.

Another object of the present invention is to provide a surgical staple extractor which employs cams to controllably spread the jaws.

Yet another object of the present invention is to provide a surgical staple extractor which employs jaws and an anvil which are securely retained in relation to a gripping portion including a pair of handles.

Briefly, and in accordance with the foregoing, the present invention envisions a surgical staple extractor which includes a pair of handles and a pair of spaced-apart jaws and an anvil associated with the handles. The handles move the anvil and the jaws in a scissor action to transfer forces from the anvil and jaws to a staple retained therebetween in order to mechanically deform or reform the staple for extraction from a patient. The extractor also includes cams disposed between the jaws and the anvil for spreading or displacing the jaws outwardly when the anvil jaws and handles are operated. Actuation of the gripping portion results in moving the anvil and jaws with the cams interacting between the anvil and jaws for displacing the jaws outwardly in relation to the anvil for promoting deformation of the staple in a removal path approximating the entry path thereby disengaging the staple from the patient.

BRIEF DESCRIPTION OF THE DRAWINGS

The organization and manner of the structure and operation of the invention, together with further objects and advantages thereof, may be understood by reference to the following description taken in connection with the accompanying drawings, wherein like reference numerals identify like elements, and in which:

FIG. 1 is a perspective view of a surgical staple extractor of the present invention positioned for extracting staples from a surgical site;

FIG. 2 is an exploded, partial fragmentary, perspective view of a surgical staple extractor of the present invention in which two jaws and an anvil of the extractor are removed from a gripping portion of the extractor;

FIG. 3 is a side elevational view of the extractor as shown in FIG. 1 in use for removal of staples;

FIG. 4 is a side elevational view of the extractor as shown in FIG. 3 in which the anvil and jaws have been operated to deform the staple positioned therebetween;

FIG. 5 is a bottom plan view taken along line 5—5 in FIG. 3 of the jaws and anvil of the extractor;

FIG. 6 is a bottom plan view taken along line 6—6 in FIG. 4 showing camming action produced by the cams positioned between each jaw and a corresponding portion of the anvil;

FIGS. 7-11 provide a progression of views showing a staple being reformed during a..staple extraction operation using an extractor of the present invention;

FIG. 7A shows an enlarged, partial fragmentary, cross-sectional view taken along line 7A—7A in FIG. 5 showing abutting engagement of the anvil and cams;

FIG. 11A shows an enlarged, partial fragmentary, cross-sectional view taken along line 11A—11A in FIG. 6 showing the cam action of the anvil and cams;

DESCRIPTION OF THE PREFERRED EMBODIMENT

Figure 12:
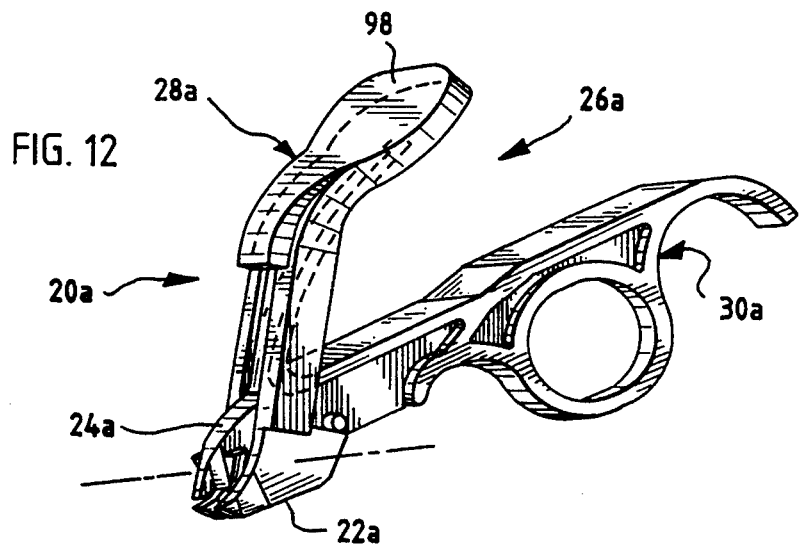
FIG. 12 is a perspective view of another form of the extractor of the present invention.

While the invention may be susceptible to embodiment in different forms, there is shown in the drawings, and herein will be described in detail, embodiments with the understanding that the present description is to be considered an exemplification of the principles of the invention and is not intended to limit the invention to that as illustrated and described herein.

FIG. 1 provides a perspective view of a surgical staple extractor 20 of the present invention. The extractor 20 includes a pair of spaced-apart jaws 22 and an anvil 24 positioned intermediate the jaws 22 and displaceable relative to the jaws 22. The jaws 22 and the anvil 24 are attached to moving means 26. As shown in FIGS. 1-4, the moving means 26 includes an upper handle 28 and a lower handle 30 spaced apart from the upper handle 28. The upper and lower handles 28, 30 are operated to produce a scissoring action with the anvil 24 and jaws 22. A living hinge 32 is integrally formed with and extending between the two handles 28, 30 to define a pivot location. With reference to FIGS. 1, 3, and 4, the extractor 20 is used to extract a staple 34 from a surgical site 36 on a patient. Staples 34 straddle a healing incision 38 in the surgical site 36 to secure edges of the incision together to facilitate healing. The extractor 20 is positioned with a tip portion 40 of each jaw 22 inserted between the patient's skin 42 and a crown 44 of the staple 34. The handles 28, 30 are then actuated to rotate or scissor the anvil 24 between the jaws 22 so that a beak portion 46 of the anvil contacts an upper surface of the crown 44.

FIG. 3 shows the extractor 20 positioned prior to removal of a staple prior to actuating the handles 28, 30. FIG. 4 provides a view of the extractor 20 with handles fully actuated, flexing the living hinge 32, and moving or fully rotating the anvil 24 relative to the jaws 22. As will be described in greater detail hereinbelow with regard to FIGS. 7-11, the movement of the anvil 24 and jaws 22 extracts the staple 34 from the surgical site 36 in a path approximating the original insertion path.

The present invention employs novel cam means 48 provided between the jaws 22 and the anvil 24. The cam means 48 is shown generally in FIGS. 2, 5, 6, 7A and 11A. As shown in the embodiment of FIGS. 1-6, and in greater detail in FIGS. 7A and 11A, the cam means 48 includes sloped protrusions 50 projecting inwardly from a surrounding inboard surfaces 52 of each of the jaws 22. The protrusions 50 provide angular sloped surfaces 53 which extend inwardly toward the anvil 24 having a maximum projection dimension generally towards a bottom edge 54 of the jaw 22. As shown in FIG. 5, in the pre-actuated position (see FIG. 3) a crest 56 of the protrusions 50 are positioned opposite each other. As will be described in greater detail hereinbelow, and as shown in FIGS. 7A and 11A, actuating the extractor 20 drives the anvil 24 and the jaws 22 relative to each other with outside surfaces 58 of the anvil 24 proximate the crests 56 contacting the crests 56 and urging the jaws 22 outwardly. Progressive scissoring movement of the jaws 22 and anvil 24 engaging the crests 56 of the protrusions 50 and the surface 58 provides a controlled positive camming action spreading the jaws 22 outwardly away from the anvil 24 before driving the staple between the jaws 22 and anvil 24 (see, FIGS. 6, 11 and 11A).

Spreading action of the jaws 22 outwardly away from the anvil is facilitated by the outwardly flexible characteristic of the jaws 22. As shown in the embodiment of FIGS. 1-6, the jaws and anvil 22, 24 are attached to the handles 28, 30 in a novel manner. As shown in FIG. 2, the jaws and anvil 22, 24 are formed independent of the handles 28, 30 which are formed integral with the living hinge 32. Slots 60 are formed in the handles 28, 30 in an area proximate to the living hinge 32. Root portions 62 are provided on ends of the jaws 22 and anvil 24, which roots 62 are sized and dimensioned for cooperative engagement with the slots 60.

Insertion of the roots 62 into the corresponding slots 60 directly structurally integrates or ties the corresponding jaw 22 and anvil 24 to the respective handle 28, 30. In other words, the jaws 22 are directly implanted in the upper handle 28 and the anvil 24 is directly implanted in the lower handle 30 by use of the roots 62 and slots 60. The structure for attaching the jaws 22 and anvil 24 is important such that dissimilar materials may be used for the handles 28, 30 and jaws and anvil 22, 24. As previously discussed, and as more clearly shown in FIGS. 3 and 4, actuation of the upper handle 28 moves the jaws 22 by way of the engagement of the corresponding roots 62 in the associated slots 60, whereas the anvil 24 is actuated by engagement of the corresponding roots 62 and the associated slots 60.

FIGS. 5 and 6 show bottom plan views of the jaws 22 and anvil 24 in a relaxed state (FIG. 5) and in a fully actuated state (FIG. 6). As shown in FIG. 5, the jaws 22 are relaxed with the crest 56 of each protrusion 50 disengaged from the opposing outside surfaces 58 of the anvil 24.

The bottom view of FIG. 6 corresponds to the side view of FIG. 4, such that the jaws and anvil 22, 24 have been actuated for the removal of a staple. When the jaws and anvil 22, 24 are actuated, the sloped surfaces 53 of the protrusions 50 abut the outside surfaces 58 of the anvil 24. With the crests 56 abutting the anvil 24, driving forces between the slope 53 of the crests 56 and the anvil 24 cams the jaws 22 outwardly at a deflection angle 63. The angle or amount of deflection 63 is limited by guides 64 which extend from the moving means 26, generally from the lower handle 30. The guides 64 abut a central body portion 66 of the jaws 22 to limit the outward deflection. As shown in FIG. 6, continued relative movement of the jaws 22 and anvil 4 will result in an outboard surface 68 of a central body portion 66 of the jaw abutting a corresponding guide 64 thereby limiting deflection of the jaws.

Turning now to the progression of views shown in FIGS. 7–11 which show a staple being reformed during a staple extraction operation using the extractor of the present invention. As shown in FIG. 7, the staple 34 is positioned in a surgical site 36 with a crown 44 positioned above a surface 42 and a pair of legs 69 extending through the surface 42 to hold together an incision 38. The staple extractor 20 is positioned with the tip portions 40 of the jaws 22 below the crown 44 and a beak 46 of the anvil 24 positioned on a top surface of the crown 44. FIG. 7A provides additional detail showing the abutting engagement of the anvil 24 and the protrusions 50 of the cams 48. As shown in FIG. 7A, corresponding surfaces of the anvil and protrusions ride against each other upon activation of the jaws and anvil. As these surfaces ride against each other, the symmetrical dimensional differences of the cams produce a camming action to outwardly deflect the jaws.

In FIG. 8 the moving means 26 (not shown in FIG. 8) has been actuated to move the anvil and jaws 24, 22 creating an upward movement of the jaws 22 (as indicated by arrow 70) and a downward movement of the anvil 24 (as indicated by arrow 71). The sloped surfaces 53 of the protrusions 50 of the cam means 48 engage the corresponding outside surfaces 58 of the anvil 24. The camming action of the protrusions 50 deflects the jaws 22 outwardly from the anvil 24. While the camming action is outwardly deflecting the jaws 22 relative to the anvil, the staple 34 is being reformed between the tips 40 and beak 46.

Camming action by the cams 48 promotes positive progressive outward deflection independent of the potential deflecting effects of the staple as it is reformed. In other words, the cams 48 positively produce the deflection of the jaws 22 and the staple is formed around the spaced apart cammed position of the jaws. The progressive outward deflection of the jaws 22 results in a more desirable reforming of the staple 34 compared to prior art staple extractors.

Continued application of force and movement of the jaws 22 (70) and anvil 22 (71) initiates reforming or bending of a central area 74 of the crown 44. By bending the central area 74 of the crown 44, the legs 69 are withdrawn from the surgical site 36 through a generally curved extraction path 76. The cam action of the protrusions 50 positions the tips 40 of the jaws 22 outwardly relative to the anvil 24 thereby promoting the bending of the central area 74 in a broad curve. The broad curve will be seen in greater detail with reference to FIGS. 9, 10 and 11.

In FIG. 9, the tip 40 of the jaws 22 are approximately horizontally aligned with the beak 46 of the anvil 24 (see reference line 78). At this position, the jaws 22 have deflected a maximum outward dimension (as indicated by reference line 80). Continued application of force (70), (71) to the jaws and anvil 22, 24 will further downwardly deform the central area 74 of the staple 34 in the large curved arc and upwardly move the legs 69 through the extraction path 76. Further, a knee 82 of the legs 69 is at a maximum horizontal outward extension (as indicated by arrow 84) at a position where the knee 82 of each leg 69 is withdrawn from the surface 42.

In FIGS. 10 and 11, the jaws 22 and anvil 24 continue to be actuated such that a dimension (as indicated by dimension arrow 86) increases relative to FIG. 9. In FIG. 10, the staple 34 is nearly completely extracted from the surgical site 36. In FIG. 11, the tips of the legs 69 are fully extracted from the skin with the central area 74 of the staple being curved in a gentle curve which is unlikely to damage the healing incision 38. FIG. 11A shows the resulting position of the sloped surfaces 53 of the cams 48 relative to the anvil 24.

As noted above, the initial controlled curving of the central area 74 is initiated by the cam means 48 such that the subsequent forming steps (FIGS. 10 and 11) follow the established reforming path 76. In other words, since the cam means 48 initiates and establishes a deforming path 76 for the staple 34 the staple is removed in a more desirable manner than prior art devices. The prior art devices generally resulted in a more pointed tip in the central area 74 and less control in the reforming of the staple since these devices lacked cam means.

Figure 18:
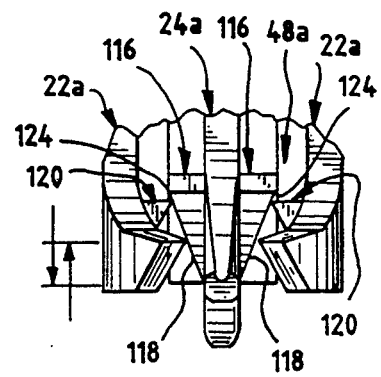
FIG. 18 is an enlarged, front elevational view taken along line 18—18 in FIG. 17 showing outward displacement of the jaws relative to the anvil by operation of the cams disposed therebetween.

Turning now to another embodiment of the present invention as shown in FIGS. 12 and 18, reference will be had to like elements using identical reference numerals with the addition of an alphabetic suffix. For example, the extractor as shown in FIG. 12 is referred to by reference numeral "a".

Figure 15:
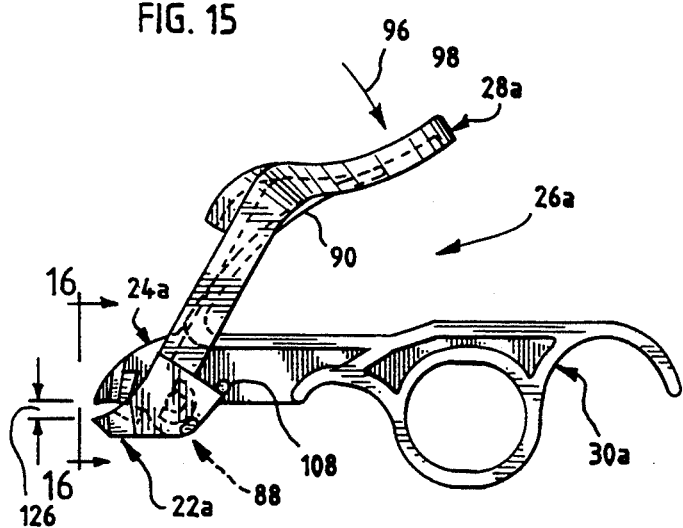
FIG. 15 is a side elevational view of the extractor as shown in FIG. 12 prior to activating the jaws and anvil.
Figure 17:
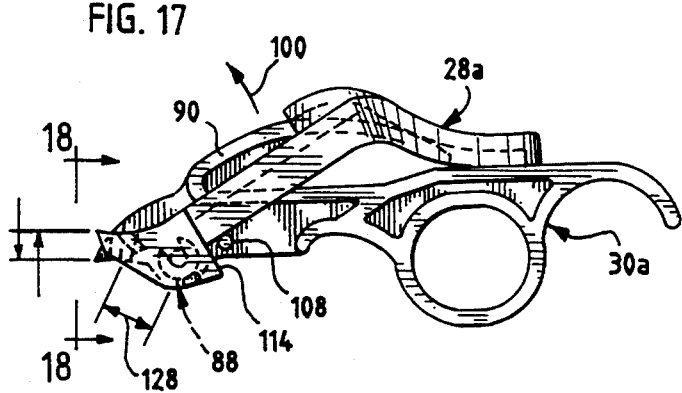
FIG. 17 is a side elevational view of the extractor as shown in FIG. 15 in which the upper handle has been actuated against a biasing member to actuate the jaws and anvil.

The extractor has moving means 26a which includes an upper handle 28a and a lower handle 30a. The handles 28a, 30a interact by way of arcuate movement means 88 integrally formed on the handles. The lower handle 30a includes a biasing member 90 which engages a channel 92 on an underside 94 of the upper handle 28a. The arcuate movement means 88 retains the jaws 22a in a desired position relative to the anvil 24a and promotes relative movement of the jaws 22a and anvil 24a. With reference to FIGS. 15 and 17, a downward force (as indicated by arrow 96) is applied to a grip section 98 of the upper handle 28a to move the jaws 22a relative to the anvil 24a. The downward force (96) compresses the return spring 90 towards the lower handle 30a in opposition to its preformed-shape. Compression of the return spring 90 creates a return force (as indicated by arrow 100) which acts against the upper handle 28a to open the jaws and anvil 22a, 24a.

Figure 13:
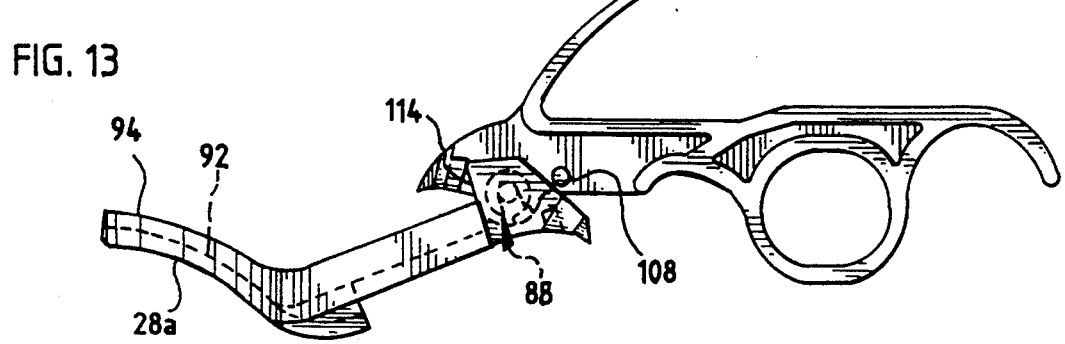
FIG. 13 is a side elevational view of the extractor as shown in FIG. 12 in which the gripping portion includes an upper handle assembled on an axle formed on a lower handle and in which the upper handle is positioned prior to rotation into the position as shown in FIG. 12.
Figure 14:
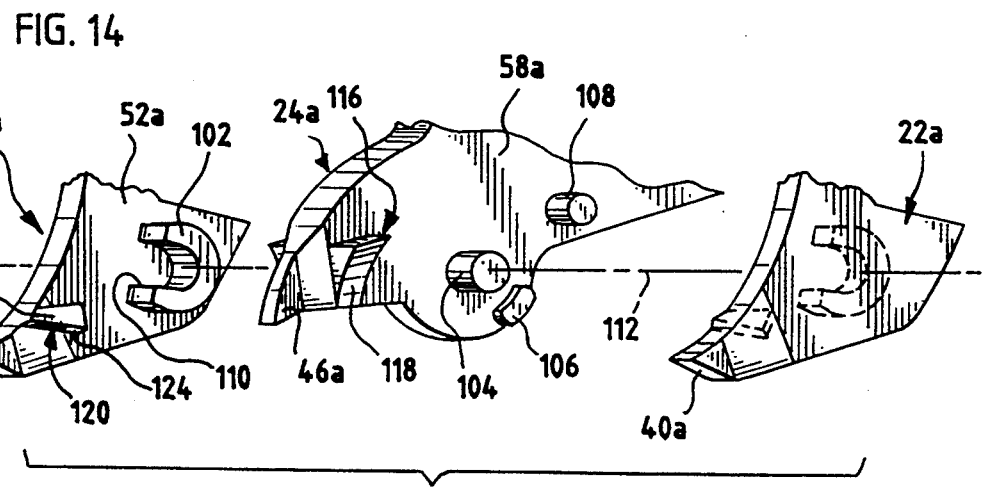
FIG. 14 is an exploded, partial fragmentary, perspective view of a head of the extractor as shown in FIG. 12 showing enlarged details of the cams between the jaws and the anvil.

The arcuate movement means 88a, as more clearly shown in FIG. 14, includes a U-shaped journal 102 formed on an inboard surface 52a of each of the jaws 22a, 22a which operatively mates with an axle 104 and is retained thereon by a retaining nub 106 and a stop post 108. As can be seen in FIG. 13, the upper handle 28a is attached to the lower handle 30a by sliding the axle 104 extending from each of the corresponding outside surfaces 58a of the anvil 24a past a mouth 110 and into engagement with the corresponding U-shaped journal 102. The upper handle 28a is rotated about a central axis 112 extending through the axles 104 so that the return spring 90 mates in the channel 92. In positioning the upper handle 28a, a limiting shoulder 114 must be forced past the stop post 108. Once the limiting shoulder 114 is forced past the stop 108 the jaws 22a are prevented from moving beyond a maximum open position as shown in FIG. 15. Additionally, once the upper handle 28a is positioned as shown in FIGS. 12 and 15, the retaining nub 106 retains the U-shaped journal 102 in close engagement with the axle 104 to provide smooth arcuate operation in the scissoring action of the extractor 20a.

Figure 16:
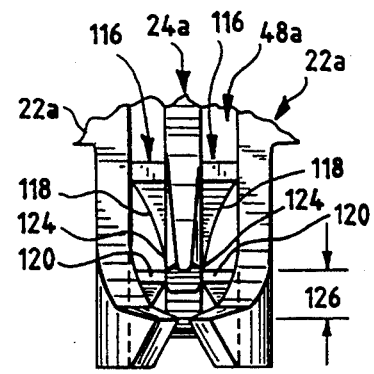
FIG. 16 is an enlarged partial fragmentary front elevational view, taken along line 16—16 in FIG. 15.

FIG. 14 provides an enlarged, exploded detail view of the cam means 48a which is further shown in operation in FIGS. 16 and 18. The cam means of this embodiment include elements on both the anvil 24a and the jaws 22a. The anvil 24a includes an inner cam element 116 which extends outwardly towards a corresponding jaw 22a from the outside surface 58a of the anvil 24a. The inner cam element 116 includes a sloped face 118. Each of the inner cam elements 116 operate in conjunction with a corresponding developed cam element 120 extending inwardly from an inboard surface 52a of the corresponding jaw 22a towards the anvil 24a. The developed cam element 120 has a operating face 122 and edge 124. The inner cam elements 116 are retained in cooperative association with the corresponding developed cam elements 120 by the retaining engagement of the rotating means 88 as described hereinabove.

FIG. 16 shows an enlarged, partial fragmentary front elevational view of the jaws 22a and anvil 24a in the position as shown in FIG. 15. As shown in FIG. 16, the cam means 48a have not been operated by movement of the jaws 22a relative to the anvil 24a and as such the jaws 22a have not been moved outwardly from the anvil 24a. Also, the tips 40a are spaced away from the beak 46a a dimension as indicated by reference numeral 126.

Movement of the upper handle 28a towards the lower handle 30a operates the jaws 22a relative to the anvil 24a as shown in FIG. 17. The position of the jaws 22a and anvil 24a is shown in greater detail in the enlarged front elevational view as shown in FIG. 18. As shown in FIG. 18, operation of the cam means 48a results in the outwardly displacement of the jaws 22a away from the anvil 24a. The operation of the cam means 48a is employed to achieve the same desirable staple deforming functions as described hereinabove with reference to FIGS. 7–11. Outward deflection of the jaws 22a is limited by the structure of the arcuate movement means 88 which defines one end of a relatively short moment arm 128 between the cam means 48a and the central axis 112. In contrast, the embodiment as shown in FIGS. 1–6 has a somewhat longer moment arm 129 between the handle and the cam means 48, as such, guides 64 are provided in the first embodiment but are not necessary in the embodiment as shown in FIGS. 12–18.

The cooperative operation of the cam means 48a as shown in the exploded perspective view of FIG. 14 is described in greater detail with regard to the operating progressions shown in FIGS. 15–18. The cam means 48a operate by driving the developed cam element 120 against the inner cam element 116. As the edge 124 of the developed cam element 120 moves along the sloped face 118 of the inner cam element 116 the jaws 22a are driven positively outwardly. The inner cam elements 116 are dimensioned with a top edge 130 sufficiently spaced along the inner cam element 116 to prevent the developed cam element 120 from overshooting the top edge 130. Additionally, the stop post 108 and the lower handle 30a contact the upper handle 28a at a maximum rotation position. (See FIG. 17).

Figure 19:
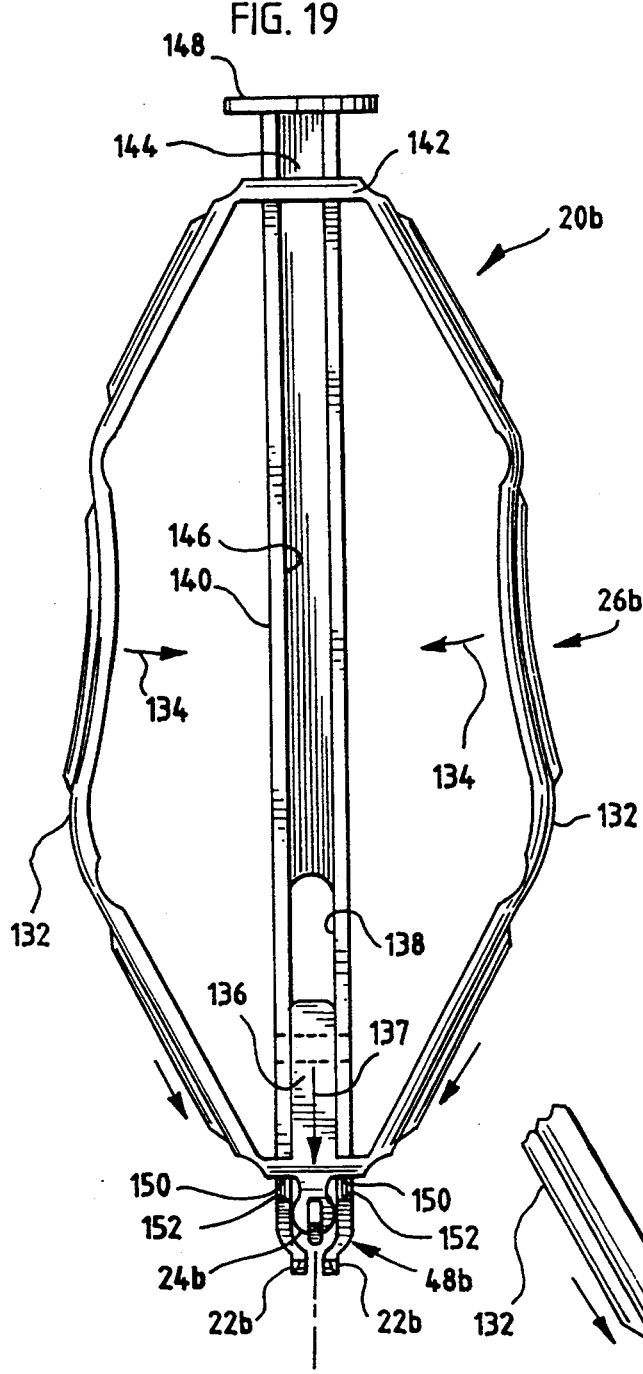
FIG. 19 is a front elevational view of an alternate embodiment of the extractor of the present invention.
Figure 20:
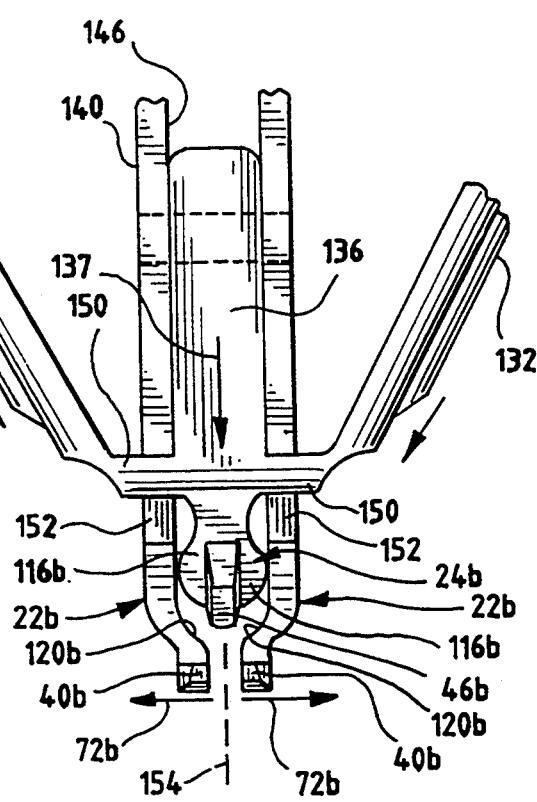
FIG. 20 is an enlarged, partial fragmentary, elevational view of the anvil and jaws of the alternate embodiment as shown in FIG. 19.

Turning now to an additional embodiment of the present invention, a linearly displaced anvil 24b and jaw 22b configuration is shown in FIGS. 19 and 20. The extractor 20b includes moving means 26b comprising two opposed compressible articulated grips 132 attached to the anvil 24b. Compression of the grips 132 inwardly (as indicated by arrow 134) drives a linear displacement segment 136 to which the anvil 24 is attached linearly (as indicated by arrow 137) along a guide slot 138 formed in a beam structure 140. An upper joining end 142 of the articulated grips 132, 132 includes a tongue 144 which rides in a guide channel 146 of the beam structure 140. Upward movement of the joining end 142 is limited by a stop 148. As such when the joining end 142 abuts the stop 148, continued inward compression (134) of the articulated grips 132 drives the linear displacement means 136 downwardly along the slot 138. The articulated grips 132 attached to the linear displacement means 136 defining cross members 150 which ride in a limiting notch 152 to limit movement of the anvil 124b between the jaws 22b. The cam means 48b of the extractor 20b include an inner cam element 116b outwardly projecting from the sides of the anvil 24b and outer cam elements 120b formed by curving the jaws 22a inwardly towards a central axis.

In use, the extractor 20b engages a staple generally at the tips 40b of the jaws 22b whereupon the grips 132 are inwardly compressed (134) to drive the anvil 24b downwardly (137) along the central axis 154. The cam protrusions 116b work against the corresponding inner cam elements 120b to drive the jaws outwardly 72b. In this regard, the extractor 20b functions to reform or deform a surgical staple in the manner as shown in the progressions of FIGS. 7–11.

While preferred embodiments of the present invention is shown and described, it is envisioned that those skilled in the art may devise various modifications of the present invention without departing from the spirit and scope of the appended claims. The invention is not intended to be limited by the foregoing disclosure.

The Invention Claimed Is:

1. A surgical staple extractor comprising:
 a pair of jaws;
 an anvil located intermediate and displaceable relative to said jaws;
 a gripping portion attached to said anvil and said jaws for actuating said jaws and anvil;
 cam means extending from at least one of said jaws and said anvil and abutting a corresponding portion of the other of said jaws and anvil for positively displacing said jaws outwardly relative to said anvil when said anvil and jaws are actuated, such that upon actuation of said gripping portion said cam means interacts between said anvil and said jaws for positively camming said jaws outwardly in relation to said anvil for promoting controlled deformation of said staple to disengage the staple from a patient.

2. A surgical staple extractor as recited in claim 1, wherein said cam means include a cam protrusion on each of said jaws, each cam protrusion extending inwardly from each jaw for abutting a corresponding surface of said anvil.

3. A surgical staple extractor as recited in claim 1, wherein said cam means include an inner cam element depending from each side of said anvil and a developed cam element depending from an associated portion of a corresponding jaw, each of said inner cam elements interacting with a corresponding one of said developed cam elements upon moving said anvil relative to said jaws for producing a camming action to move said jaws outwardly relative to said anvil.

4. A surgical staple extractor as recited in claim 1, further comprising a pair of guides extending distally from said gripping portion, each of said guides being positioned outboard relative to a corresponding one of said jaws for limiting the outward displacement of said jaws.

5. A surgical staple extractor as recited in claim 1, further comprising means for relative arcuate movement of said anvil and jaws, said arcuate movement means being attached to said gripping portion, such that relative arcuate displacement of said anvil and said jaws positions said cam means against opposed surfaces of said jaws and said anvil for positively outwardly displacing said jaws relative to said anvil.

6. A surgical staple extractor as recited in claim 1, wherein said gripping portion linearly displaces said anvil relative to said jaws, such that linear displacement of said anvil and said jaws positions said cam means against opposed surfaces of said jaws and said anvil for outwardly displacing said jaws relative to said anvil as said anvil moves linearly therebetween.

7. A surgical staple extractor as recited in claim 6, wherein said cam means include a cam protrusion on each side of said anvil, said cam protrusions being positioned for engaging an associated surface of a corresponding jaw upon linear displacement of said anvil therebetween.

8. A surgical staple extractor comprising:
upper and lower spaced apart handles, said handles being operatively attached action;
two spaced apart jaws being attached to said upper handle, a portion of each of said two jaws being positionable beneath a surgical staple;
an anvil attached to said lower handle and positioned intermediate said jaws and displaceable relative to said two spaced apart jaws, a portion of said anvil being positionable above a surgical staple; and
a root extending from each of said jaws and said anvil, each root being embedded in a corresponding slot formed in said handles, said root portions being retained in said slots such that forces are transferred from said handles to said jaws and anvil upon actuation of sasid upper and lower spaced apart handles producing a scissoring of said jaws and anvil.

9. A surgical staple extractor as recited in claim 8, further comprising: a pair of cams, one each of said pair of cams extending from at least one of said anvil and said two jaws, said cams interacting with the other of said anvil and said two jaws for moving each of said jaws outwardly relative to to said anvil when said two jaws and said anvil are relatively displaced.

10. A surgical staple extractor comprising:
upper and lower spaced apart handles, said handles being operatively attached to provide a scissoring action;
two spaced apart jaws being operatively attached to said upper handle, a portion of each of said two jaws being positionable beneath a surgical staple;
an anvil operatively attached to said lower handle and positioned intermediate said jaws and displaceable relative to said two spaced apart jaws, a portion of said anvil being positionable above a surgical staple; and
a pair of cams, one each of said pair of cams extending from one of said anvil and said two spaced apart jaws and abutting the other of said anvil and said two spaced apart jaws, said cams interacting with said anvil and said jaws for moving each of said jaws outwardly relative to said anvil when said jaws and said anvil are actuated.

11. A surgical staple extractor as recited in claim 10, further comprising a living hinge integrally formed with and extending between said upper and lower spaced apart handles.

12. A surgical staple extractor as recited in claim 10, further comprising a pair of guides extending distally from said hinge and upper and lower handles, each of said guides being positioned outboard relative to a corresponding one of said jaws for limiting the outward displacement of said jaws.

13. A surgical staple extractor as recited in claim 10, wherein said cams include a cam protrusion on each of said jaws, each cam protrusion extending inwardly from each jaw towards said anvil for abutting a corresponding surface of said anvil.

14. A surgical staple extractor as recited in claim 10, wherein each of said cam means include an inner cam element depending from each side of said anvil and a developed cam element depending from an associated portion of a corresponding jaw, each of said inner cam elements interacting with a corresponding one of said developed cam elements upon moving said anvil relative to said jaws for producing a camming action to move said jaws outwardly relative to said anvil.

15. A surgical staple extractor as recited in claim 10, further comprising said upper handle being arcuately displaceable relative to and associated with said lower handle.

16. A surgical staple extractor as recited in claim 15, further comprising a biasing member depending from one of said upper and lower handles, said biasing member being positioned between said upper and lower handles for oppositely biasing said upper and lower handles to facilitate a return function of the scissoring action of the extractor.

17. A surgical staple extractor as recited in claim 10, further comprising: a root extending from each of said jaws and said anvil, each root being imbedded in a corresponding slot formed in said handles, said root portions being retained in said slots such that forces are transferred from said handles to said jaws and anvil upon actuation of sasid handles.

18. A surgical staple extractor comprising:
an upper handle and a lower handle formed of a plastic material and defining a living hinge integrally formed therebetween;
two spaced apart jaws being operatively attached to said upper handle, a root portion of each of said jaws being retained on said upper handle;
an anvil operatively attached to said lower handle independant of said jaws positioned for relative movement intermediate said jaws, a root portion of said anvil being retained on said lower handle, such that operation of said upper and lower handles scissors said anvil between said jaws whereby said anvil and jaws are relatively driven to deform a staple therebetween.

19. A surgical staple extractor as recited in claim 18, further comprising:
   a pair of cam means, one each of said pair of cam means being disposed on a surface of said jaws facing said anvil, said anvil interacting with said cam means for moving said jaws outwardly when said anvil is driven between said jaws upon actuation of said handles, such that actuation of said handles produces a scissoring action in said jaws and anvil, said jaws are moved outwardly and upwardly relative to said anvil which moves downwardly and centrally against said cam portions for disengaging a staple from a patient.

\* \* \* \* \*

UNITED STATES PATENT AND TRADEMARK OFFICE
CERTIFICATE OF CORRECTION

PATENT NO. : 5,451,231
DATED : September 19, 1995
INVENTOR(S) : Richard Rabenau and Larry L. Young It is certified that error appears in the above-indentified patent and that said Letters Patent is hereby corrected as shown below:

Column 1, Line 64 "patient' issue" should read — patient's tissue —

Column 1, Line 66 "frommthe" should read — from the —

Column 5, Line 17 "anvil 4" should read — anvil 24 —

Column 8, Lines 56-57 "portionof theother" should read
— portion of the other —

Column 9, Line 55 "sasid" should read — said —

Column 9, Lines 62-63 "said jaws" should read —said two jaws —

Column 9, Line 63 "relative to to" should read —relative to —

Column 10, Line 57 "sasid" should read —said —

Signed and Sealed this

Nineteenth Day of March, 1996

*Attest:*

BRUCE LEHMAN

*Attesting Officer*  *Commissioner of Patents and Trademarks*